United States Patent
Yue et al.

(10) Patent No.: US 10,815,303 B2
(45) Date of Patent: Oct. 27, 2020

(54) FUSION PROTEIN FOR RESTORING THE FUNCTIONS OF FAILING IMMUNE CELLS AND APPLICATION THEREOF

(71) Applicant: SHANGHAI BIOMED-UNION BIOTECHNOLOGY CO., LTD, Pudong New District, Shanghai (CN)

(72) Inventors: Xilian Yue, Shanghai (CN); Gentao Liu, Shanghai (CN); Guoxiang Wu, Shanghai (CN)

(73) Assignee: Shanghai Biomed-Union Biotechnology Co., Ltd., Pudong New District, Shanghai (CN)

( * ) Notice: Subject to any disclaimer, the term of this patent is extended or adjusted under 35 U.S.C. 154(b) by 0 days.

(21) Appl. No.: 16/496,348

(22) PCT Filed: Apr. 7, 2017

(86) PCT No.: PCT/CN2017/079679
§ 371 (c)(1),
(2) Date: Sep. 20, 2019

(87) PCT Pub. No.: WO2018/176505
PCT Pub. Date: Oct. 4, 2018

(65) Prior Publication Data
US 2020/0040080 A1    Feb. 6, 2020

(30) Foreign Application Priority Data
Mar. 29, 2017    (CN) .......................... 2017 1 0197757

(51) Int. Cl.
| C07K 16/28 | (2006.01) |
| C07K 14/55 | (2006.01) |
| A61K 39/395 | (2006.01) |
| A61K 38/20 | (2006.01) |
| A61K 39/00 | (2006.01) |

(52) U.S. Cl.
CPC .......... *C07K 16/2818* (2013.01); *C07K 14/55* (2013.01); *A61K 2039/505* (2013.01); *C07K 2319/33* (2013.01)

(58) Field of Classification Search
None
See application file for complete search history.

(56) References Cited

U.S. PATENT DOCUMENTS

| 2013/0039911 A1* | 2/2013 | Bedi ................... C07K 14/495 424/134.1 |
| 2017/0037131 A1* | 2/2017 | Bernett .............. C07K 16/2812 |
| 2017/0362321 A1* | 12/2017 | Campbell ............ C07K 16/468 |
| 2018/0326010 A1* | 11/2018 | Codarri Deak .... A61K 47/6891 |

FOREIGN PATENT DOCUMENTS

| CN | 101365799 A | 2/2009 |
| CN | 101426532 A | 5/2009 |
| CN | 103768596 A | 5/2014 |
| CN | 103965361 A | 8/2014 |
| CN | 104024276 A | 9/2014 |
| CN | 104185681 A | 12/2014 |
| CN | 104334573 A | 2/2015 |
| CN | 105263521 A | 1/2016 |
| CN | 105531288 A | 4/2016 |
| CN | 105828834 A | 8/2016 |
| CN | 105874061 A | 8/2016 |
| CN | 106132436 A | 11/2016 |
| WO | WO 2016/027764 A1 | 2/2016 |

OTHER PUBLICATIONS

Chen et al., Biochem Biophys Res Comm (2016) 480, 160-165.*
Giuliani et al. Oncotarget, 2017, vol. 8, (No. 14), pp. 24031-24044.*
Vari et al. (Blood. 2018;131(16):1809-1819).*
GenBank, AAH66254.1 Interleukin 2 [*Homo sapiens*], Mar. 6, 2007.
GenBank, 5WT9_L Chain L, Ligh Chain of Nivolumab, Jan. 15, 2018.

* cited by examiner

*Primary Examiner* — Ilia I Ouspenski
(74) *Attorney, Agent, or Firm* — Muncy, Geissler, Olds & Lowe, P.C.

(57) ABSTRACT

A fusion protein for restoring functions of failing immune cells and application thereof. The fusion protein has a functional area for recognizing the failing immune cell and a functional area for conducting activation and amplification on the failing immune cell. The two functional areas are connected through a non-functional amino acid fragment with a certain length. The functional area for recognition uses the immune checkpoint specific antibody to recognize a phenotypic receptor of failing immune cells. The functional area for conducting activation and amplification adopts the cytokine or functionally-similar mutants, a ligand of the phenotypic receptor or functionally-similar mutants or an activating antibody to activate failing immune cells. The fusion protein recognizes failing immune cells, conducts activation and amplification on recognized failing immune cells, restores functions of killing antigen positive cells by the immune cells, and enhances inhibition of tumor growth and virus infection control.

4 Claims, 4 Drawing Sheets

Specification includes a Sequence Listing.

LaneA:fusion-protein(reduced)
LaneB:fusion-protein(non-reduced)
MK: Molecular weight marker

SEQUENCE LISTING

```
<160> NUMBER OF SEQ ID NOS: 24

<210> SEQ ID NO 1
<211> LENGTH: 122
<212> TYPE: PRT
<213> ORGANISM: Artificial Sequence
<220> FEATURE:
<223> OTHER INFORMATION: PD-1

<400> SEQUENCE: 1

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg
        115                 120

<210> SEQ ID NO 2
<211> LENGTH: 142
<212> TYPE: PRT
<213> ORGANISM: Artificial Sequence
<220> FEATURE:
<223> OTHER INFORMATION: PD-L1

<400> SEQUENCE: 2

Pro Tyr Asn Lys Ile Asn Gln Arg Ile Leu Val Val Asp Pro Val Thr
```

-continued

```
1               5                   10                  15
Ser Glu His Glu Leu Thr Cys Gln Ala Glu Gly Tyr Pro Lys Ala Glu
                20                  25                  30

Val Ile Trp Thr Ser Ser Asp His Gln Val Leu Ser Gly Lys Thr Thr
                35                  40                  45

Thr Thr Asn Ser Lys Arg Glu Glu Lys Leu Phe Asn Val Thr Ser Thr
        50                  55                  60

Leu Arg Ile Asn Thr Thr Thr Asn Glu Ile Phe Tyr Cys Thr Phe Arg
65                  70                  75                  80

Arg Leu Asp Pro Glu Glu Asn His Thr Ala Glu Leu Val Ile Pro Glu
                85                  90                  95

Leu Pro Leu Ala His Pro Pro Asn Glu Arg Thr His Leu Val Ile Leu
                100                 105                 110

Gly Ala Ile Leu Leu Cys Leu Gly Val Ala Leu Thr Phe Ile Phe Arg
                115                 120                 125

Leu Arg Lys Gly Arg Met Met Asp Val Lys Lys Cys Gly Ile
                130                 135                 140
```

<210> SEQ ID NO 3
<211> LENGTH: 301
<212> TYPE: PRT
<213> ORGANISM: Artificial Sequence
<220> FEATURE:
<223> OTHER INFORMATION: TIM-3

<400> SEQUENCE: 3

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
                20                  25                  30

Asn Ala Tyr Leu Pro Cys Phe Tyr Thr Pro Ala Ala Pro Gly Asn Leu
                35                  40                  45

Val Pro Val Cys Trp Gly Lys Gly Ala Cys Pro Val Phe Glu Cys Gly
        50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
                115                 120                 125

Ile Lys Pro Ala Lys Val Thr Pro Ala Pro Thr Leu Gln Arg Asp Phe
                130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
                180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
                210                 215                 220

Lys Trp Tyr Ser His Ser Lys Glu Lys Ile Gln Asn Leu Ser Leu Ile
```

```
                225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
                260                 265                 270

Glu Val Glu Glu Pro Asn Glu Tyr Tyr Cys Tyr Val Ser Arg Gln
                275                 280                 285

Gln Pro Ser Gln Pro Leu Gly Cys Arg Phe Ala Met Pro
                290                 295                 300

<210> SEQ ID NO 4
<211> LENGTH: 115
<212> TYPE: PRT
<213> ORGANISM: Artificial Sequence
<220> FEATURE:
<223> OTHER INFORMATION: CTLA-4

<400> SEQUENCE: 4

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile
        115

<210> SEQ ID NO 5
<211> LENGTH: 326
<212> TYPE: PRT
<213> ORGANISM: Artificial Sequence
<220> FEATURE:
<223> OTHER INFORMATION: LAG-3

<400> SEQUENCE: 5

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110
```

```
Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu
                325

<210> SEQ ID NO 6
<211> LENGTH: 440
<212> TYPE: PRT
<213> ORGANISM: Artificial Sequence
<220> FEATURE:
<223> OTHER INFORMATION: Anti-PD-1 antibody

<400> SEQUENCE: 6

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140
```

```
Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
195                 200                 205

Lys Arg Val Glu Ser Lys Tyr Gly Pro Pro Cys Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
            325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 7
<211> LENGTH: 214
<212> TYPE: PRT
<213> ORGANISM: Artificial Sequence
<220> FEATURE:
<223> OTHER INFORMATION: Anti-PD-1 antibody

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 8
<211> LENGTH: 447
<212> TYPE: PRT
<213> ORGANISM: Artificial Sequence
<220> FEATURE:
<223> OTHER INFORMATION: Anti-PD-1 antibody

<400> SEQUENCE: 8

```
Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205
```

-continued

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 9
<211> LENGTH: 218
<212> TYPE: PRT
<213> ORGANISM: Artificial Sequence
<220> FEATURE:
<223> OTHER INFORMATION: Anti-PD-1 antibody

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 10
<211> LENGTH: 118
<212> TYPE: PRT
<213> ORGANISM: Artificial Sequence
<220> FEATURE:
<223> OTHER INFORMATION: Anti-CTLA-4 antibody

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
                100                 105                 110

Leu Val Thr Val Ser Ser
            115

<210> SEQ ID NO 11
<211> LENGTH: 108
<212> TYPE: PRT
<213> ORGANISM: Artificial Sequence
<220> FEATURE:
<223> OTHER INFORMATION: Anti-CTLA-4 antibody

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Trp Thr Phe Gly Gln Gly Thr Lys Val Glu Ile Lys
            100                 105

<210> SEQ ID NO 12
<211> LENGTH: 124
<212> TYPE: PRT
<213> ORGANISM: Artificial Sequence
<220> FEATURE:
<223> OTHER INFORMATION: Anti-PD-L1 antibody

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Pro His Phe Val Ser Gly Ser Pro Phe Gly Met Asp Val
            100                 105                 110

Trp Gly Gln Gly Gly Thr Thr Val Thr Val Ser Ser
        115                 120

<210> SEQ ID NO 13
<211> LENGTH: 106
<212> TYPE: PRT
<213> ORGANISM: Artificial Sequence
<220> FEATURE:
<223> OTHER INFORMATION: Anti-PD-L1 antibody

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 14
<211> LENGTH: 133
<212> TYPE: PRT
<213> ORGANISM: Artificial Sequence
<220> FEATURE:
<223> OTHER INFORMATION: IL-2

<400> SEQUENCE: 14
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 15
<211> LENGTH: 130
<212> TYPE: PRT
<213> ORGANISM: Artificial Sequence
<220> FEATURE:
<223> OTHER INFORMATION: IL-15

<400> SEQUENCE: 15

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
                100                 105                 110

Glu Glu Lys Asn Ile Lys Glu Phe Leu Gln Ser Phe Val His Ile Val
            115                 120                 125

Gln Met
    130

<210> SEQ ID NO 16
<211> LENGTH: 153
<212> TYPE: PRT
<213> ORGANISM: Artificial Sequence
<220> FEATURE:
<223> OTHER INFORMATION: IL-21

<400> SEQUENCE: 16

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30
```

```
Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
 50                  55                  60

Glu Asp Val Glu Thr Asn Cys Glu Trp Ser Ala Phe Ser Cys Phe Gln
 65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
130                 135                 140

Gln Lys Val Ser Thr Leu Ser Phe Ile
145                 150

<210> SEQ ID NO 17
<211> LENGTH: 254
<212> TYPE: PRT
<213> ORGANISM: Artificial Sequence
<220> FEATURE:
<223> OTHER INFORMATION: 4-1BBL

<400> SEQUENCE: 17

Met Glu Tyr Ala Ser Asp Ala Ser Leu Asp Pro Glu Ala Pro Trp Pro
1               5                  10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
 50                  55                  60

Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240
```

```
Thr Pro Glu Ile Pro Ala Gly Leu Pro Ser Pro Arg Ser Glu
                245                 250

<210> SEQ ID NO 18
<211> LENGTH: 133
<212> TYPE: PRT
<213> ORGANISM: Artificial Sequence
<220> FEATURE:
<223> OTHER INFORMATION: OX-40L

<400> SEQUENCE: 18

Met Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 19
<211> LENGTH: 460
<212> TYPE: PRT
<213> ORGANISM: Artificial Sequence
<220> FEATURE:
<223> OTHER INFORMATION: Antibody against 4-1BB

<400> SEQUENCE: 19

Met Asp Trp Thr Trp Arg Ile Leu Phe Leu Val Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Trp Met Ser Trp Val Arg Gln Ala Pro Gly Lys Gly Leu
    50                  55                  60

Glu Trp Val Ala Asp Ile Lys Asn Asp Gly Ser Tyr Thr Asn Tyr Ala
65                  70                  75                  80

Pro Ser Leu Thr Asn Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Glu Leu Thr Gly Thr Trp Gly Gln Gly Thr Met
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
```

```
                145                 150                 155                 160
Leu Val Lys Asp Tyr Phe Pro Glu Pro Val Thr Val Ser Trp Asn Ser
                    165                 170                 175
Gly Ala Leu Thr Ser Gly Val His Thr Phe Pro Ala Val Leu Gln Ser
                180                 185                 190
Ser Gly Leu Tyr Ser Leu Ser Ser Val Val Thr Val Pro Ser Ser Ser
            195                 200                 205
Leu Gly Thr Lys Thr Tyr Thr Cys Asn Val Asp His Lys Pro Ser Asn
    210                 215                 220
Thr Lys Val Asp Lys Arg Val Glu Ser Lys Tyr Gly Pro Pro Cys Pro
225                 230                 235                 240
Pro Cys Pro Ala Pro Glu Phe Leu Gly Gly Pro Ser Val Phe Leu Phe
                    245                 250                 255
Pro Pro Lys Pro Lys Asp Thr Leu Met Ile Ser Arg Thr Pro Glu Val
                260                 265                 270
Thr Cys Val Val Val Asp Val Ser Gln Glu Asp Pro Glu Val Gln Phe
            275                 280                 285
Asn Trp Tyr Val Asp Gly Val Glu Val His Asn Ala Lys Thr Lys Pro
    290                 295                 300
Arg Glu Glu Gln Phe Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                    325                 330                 335
Ser Asn Lys Gly Leu Pro Ser Ser Ile Glu Lys Thr Ile Ser Lys Ala
                340                 345                 350
Lys Gly Gln Pro Arg Glu Pro Gln Val Tyr Thr Leu Pro Pro Ser Gln
            355                 360                 365
Glu Glu Met Thr Lys Asn Gln Val Ser Leu Thr Cys Leu Val Lys Gly
    370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                    405                 410                 415
Phe Phe Leu Tyr Ser Arg Leu Thr Val Asp Lys Ser Arg Trp Gln Glu
                420                 425                 430
Gly Asn Val Phe Ser Cys Ser Val Met His Glu Ala Leu His Asn His
            435                 440                 445
Trp Thr Gln Lys Ser Leu Ser Leu Ser Leu Gly Lys
    450                 455                 460

<210> SEQ ID NO 20
<211> LENGTH: 235
<212> TYPE: PRT
<213> ORGANISM: Artificial Sequence
<220> FEATURE:
<223> OTHER INFORMATION: Antibody against 4-1BB

<400> SEQUENCE: 20

Met Glu Ala Pro Ala Gln Leu Leu Phe Leu Leu Leu Leu Trp Leu Pro
1               5                   10                  15
Asp Ile Val Met Thr Gln Ser Pro Asp Ser Leu Ala Val Ser Leu Gly
                20                  25                  30
Glu Arg Ala Thr Ile Asn Cys Lys Ser Ser Gln Ser Leu Leu Ser Ser
            35                  40                  45
Gly Asn Gln Lys Asn Trp Leu Ala Trp Tyr Gln Gln Lys Pro Gly Gln
```

```
                    50                  55                  60

Pro Pro Lys Leu Leu Ile Trp Trp Ala Ser Thr Arg Gln Ser Gly Val
65                  70                  75                  80

Pro Asp Arg Phe Ser Gly Ser Gly Ser Gly Thr Asp Phe Thr Leu Thr
                85                  90                  95

Ile Ser Ser Leu Gln Ala Glu Asp Val Ala Tyr Tyr Cys Leu Gln Tyr
                100                 105                 110

Asp Arg Asp Pro Phe Thr Phe Gly Gln Gly Thr Lys Leu Glu Ile Lys
                115                 120                 125

Arg Thr Val Ala Ala Pro Ser Val Phe Ile Phe Pro Pro Ser Asp Glu
                130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
                210                 215                 220

Pro Val Thr Lys Ser Phe Asn Arg Gly Glu Cys
225                 230                 235

<210> SEQ ID NO 21
<211> LENGTH: 120
<212> TYPE: PRT
<213> ORGANISM: Artificial Sequence
<220> FEATURE:
<223> OTHER INFORMATION: Antibody against XO-40

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
                20                  25                  30

Ala Met Ser Thr Val Arg Gln Ala Pro Gly Lys Gly Leu Glu Thr Val
                35                  40                  45

Ser Ile Ile Ser Gly Ser Gly Gly Phe Thr Tyr Tyr Ala Asp Ser Val
                50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Val Ala Pro Gly Thr Phe Asp Tyr Trp Gly Gln
                100                 105                 110

Gly Ala Leu Val Thr Val Ser Ser
                115                 120

<210> SEQ ID NO 22
<211> LENGTH: 106
<212> TYPE: PRT
<213> ORGANISM: Artificial Sequence
<220> FEATURE:
<223> OTHER INFORMATION: Antibody against XO-40

<400> SEQUENCE: 22
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Tyr Tyr Cys Gln Gln Tyr Asn Ser Tyr Pro Tyr Thr
                85                  90                  95

Phe Gly Gln Gly Thr Lys Leu Glu Ile Lys
            100                 105

<210> SEQ ID NO 23
<211> LENGTH: 589
<212> TYPE: PRT
<213> ORGANISM: Artificial Sequence
<220> FEATURE:
<223> OTHER INFORMATION: Heavy chain structural gene of fusion protein

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
210                 215                 220

Pro Glu Phe Glu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255
```

-continued

```
Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Ser Gly Gly Gly Ser Gly Gly Gly
        435                 440                 445

Gly Ser Gly Gly Gly Gly Ser Gly Ala Pro Thr Ser Ser Ser Thr Lys
450                 455                 460

Lys Thr Gln Leu Gln Leu Glu His Leu Leu Leu Asp Leu Gln Met Ile
465                 470                 475                 480

Leu Asn Gly Ile Asn Asn Tyr Lys Asn Pro Lys Leu Thr Arg Met Leu
                485                 490                 495

Thr Phe Lys Phe Tyr Met Pro Lys Lys Ala Thr Glu Leu Lys His Leu
            500                 505                 510

Gln Cys Leu Glu Glu Glu Leu Lys Pro Leu Glu Glu Val Leu Asn Leu
        515                 520                 525

Ala Gln Ser Lys Asn Phe His Leu Arg Pro Arg Asp Leu Ile Ser Asn
530                 535                 540

Ile Asn Val Ile Val Leu Glu Leu Lys Gly Ser Glu Thr Thr Phe Met
545                 550                 555                 560

Cys Glu Tyr Ala Asp Glu Thr Ala Thr Ile Val Glu Phe Leu Asn Arg
                565                 570                 575

Trp Ile Thr Phe Cys Gln Ser Ile Ile Ser Thr Leu Thr
            580                 585
```

<210> SEQ ID NO 24
<211> LENGTH: 17
<212> TYPE: PRT
<213> ORGANISM: Artificial Sequence
<220> FEATURE:
<223> OTHER INFORMATION: non-functional amino acids

<400> SEQUENCE: 24

```
Ser Gly Gly Gly Gly Ser Gly Gly Gly Gly Ser Gly Gly Gly Ser Gly
1               5                   10                  15
```

FUSION PROTEIN FOR RESTORING THE FUNCTIONS OF FAILING IMMUNE CELLS AND APPLICATION THEREOF

TECHNICAL FIELD

The present invention relates to the field of fusion protein, in particular to a fusion protein for restoring the functions of failing immune cells and application thereof.

BACKGROUND

Cancer is the most serious and common disease that threatens people's life and life quality, and chronic diseases induced by viral infection are worldwide difficulty. At present, there are various inadequacies of the clinical application of drugs for cancer, for instance, the great side effects of chemotherapeutics, drug resistance (Curr Pharm Des. 2010, 16: 3-10) easily induced by targeted drugs, low efficiency of immune checkpoint inhibitors (N Engl J Med 2012, 366: 2443-2454); and also, chimeric antigen receptor T (Car-T) cell therapy would bring about cytokine storm and high relapse rates (Curr Opin Pediatr, 2017, 29: 27-33). Hundreds of millions of people are infected with HBV (Hepatitis B Virus) in China (APJCP, 2011, 12: 1405-1408), and long-term viral infection can further lead to more severe diseases such as cirrhosis, AIDS, cervical cancer, liver cancer (PNAS 2012, 109: 1802-1829), especially there is a lack of effective drugs on the market for treating diseases caused by HBV (Clinical Science 2013, 124: 77-85). Therefore, it is the most pressing project and need in the field of medical treatment and health in China and even the world to find new drugs with high efficiency and low toxicity for the treatment of cancer and chronic viral infection, so as to reduce mortality and improve the living quality of patients.

Tumor is induced due to genetic mutation occurs during cell division of an organism and mutant cells' growth which is out of regulatory control. If the tumor cells cannot be cleared in the short term, the functional failure of antigen-specific T cell of tumor will be gradually caused (Nature Medicine 1999, 5: 677-685), so that the tolerance to the tumor will be formed, and the immune system will be no longer sensitive to the tumor cells, thereby causing the tumor to further grow and diffuse, and arising the cancer (PNAS. 2002, 99: 12293-7). The development of chronic diseases caused by viral infection is also the consequence of antigen-specific cell failure (Trends Immunol. 2014, 35: 51-60; Blood 2007, 109: 4671-4678; Cell Death and Disease 2015, 6: e1694). Studies suggest that most tumor infiltrating lymphocyte (TIL) and antiviral specific T cell express immunosuppressive receptors (PNAS 2010, 107: 7875-7880; JI 2007, 178: 2714-2720), which are in a state of failure, losing the functions of specific recognition and killing antigen-positive target cell. Exhausted T cells lose their ability to secrete cytokines, for instance, gamma interferon (IFN-γ) and the like (Blood 2013, 121: 1367-1376; J. Biomed. Biotechnol. 2011, 451694). Even if a large number of specific T cells exist in the organism, the failing immune cells cannot clear the antigen-positive target cell (J Immunol 2005; 175: 6169-6176). Phenotypically, the exhausted T cells generally highly express immunosuppression checkpoint receptors, such as programmed death receptor (PD-1), programmed death ligand (PD-L), T cell immunoglobulin 3 (Tim-3), cytotoxic T lymphocyte antigen 4 (CTLA-4), and lymphocyte activation gene 3 (Lag-3), etc. (Nat Immunol. 2011; 12: 492-9). Activation of these signaling pathways inhibits T cell's diffusion, reduces T cell's function, promotes T cell's apoptosis and causes immune tolerance (J Clin Invest. 2011, 121: 2350-2360). Therefore, activation of this group of antigen-specific immune cells allows them to restore their function of killing antigen-positive target cell, so that tumor or viral infected cells can be cleared (Trends Immunol. 2015; 36: 265-276), and the purpose of healing is ultimately achieved.

The antibody can specifically recognize the protein antigen on the surface of the target cell; the checkpoint inhibitory antibody can inhibit the immunosuppressive signal on the surface of the exhausted cell, for EMBODIMENT, the Anti-PD-1 antibody of Pembrolizumab and Nivolumab are combined with PD-1 to prevent the conduction and activation of the inhibiting signal, and to restore the function of the exhausted immune cells, which has already achieved the clinical effect of treating cancer, in particular, tumor's complete disappearance was achieved by some patients (N Engl J Med 2012, 366: 2455-2465; N Engl J Med 2012, 366: 2443-2454). However, the clinical efficacy was not satisfactory for those patients lacking effector cells (NATURE 2014, 515: 568-571), and the duration of recovery time for such T cell was short (Science 2016, 354: 1160-1165), then specific immune cells in patients' bodies quickly returned to the state of failure (Science 2016, 354: 1165-1169). Meanwhile, only blocking the inhibiting signal of T cell would not result in an increase in the amount of immune cells, while clinical effects (Nature 2014, 515: 568-571) would not be made for those patients lacking T effector cells, thereby limiting the clinical therapeutic effects.

Clinical application of leucocyte's growth factor in the treatment of tumor has a certain effect and different levels of side effects (Semin Oncol. 2015, 42: 539-548). The clinical application of interleukin 2 (IL-2) is the first immunotherapy for cancer treatment, which can completely clear tumor cells and achieve a complete cure effect for some cancer patients (Cancer 2008, 113: 293-301; JCO 2005, 23: 133-141). However, cytokines have an activating effect on all cells expressing their receptors, thereby possibly activating non-target cells, and clinical application has a series of toxic and side effects that limit its clinical application (JI 2014, 192: 5451-5458). Therefore, the clinical application range and curative effect of IL-2 are very limited at present (Immunity 2013, 38: 13-25). Activating the patient's immune system with activating Anti-4-1BB antibody (Oncology 2010, 37: 508-516) and Anti-ox-40 antibody (Cancer Science 2008 99: 361-367) also produces side effects. Similarly, T cells can be activated by activating ligands 4-1BBL and OX-40L, but neither of these effects can be directed against exhausted specific cells (J. Leukoc. Biol. 21011, 89: 989-999).

To date, there has been no protein drug that can both specifically recognize exhausted specific T cell and restore the function thereof and increase the amount thereof.

SUMMARY

The target of present invention is to overcome the defects in the prior art, and provide a fusion protein for restoring the functions of failing immune cells, which can not only recognize the failing immune cells, but also increase the amount of immune cells and restore the functions of the immune cells.

To achieve above goals, the present invention adopts the following technical solutions:

The invention provides a fusion protein for restoring the functions of failing immune cells. The fusion protein comprises a functional area for recognizing the failing immune cell and a functional area for conducting activation and amplification on the failing immune cell and the two functional areas are connected through a non-functional amino acid fragment with a certain length, so that the protein folding of two functional areas will not interfere with each other, and bifunctional features of the fusion protein are guaranteed.

To further optimize the above technical solution, technical solutions of the present invention further comprise:

Preferably, the functional area for recognizing the failing immune cells uses the immune checkpoint specific antibody to recognize a phenotypic receptor of failing immune cells; and the phenotypic receptor of failing immune cells is an immune checkpoint which has a co-inhibitory function.

Preferably, phenotypic receptors of the failing immune cells include but are not limited to PD-1, PD-L1, TIM-3, CTLA-4, LAG-3, and overexpression of such receptor genes on the surface of the immune cells results in the failure and lack of function thereof.

Preferably, the amino acid sequence of the PD-1 is as shown in SEQ ID NO: 1; the amino acid sequence of the PD-L1 is as shown in SEQ ID NO: 2; the amino acid sequence of the TIM-3 is as shown in SEQ ID NO: 3; the amino acid sequence of the CTLA-4 is as shown in SEQ ID NO: 4; the amino acid sequence of the LAG-3 is as shown in SEQ ID NO: 5.

Preferably, specific antibodies of the phenotypic receptor include but are not limited to Anti-PD-1 antibody, Anti-CTLA-4 antibody, Anti-PD-L1 antibody, Anti-TIM-3 antibody, and Anti-LAG-3 antibody, and through the combination of antibodies and receptors, on the one hand, combination and signaling between receptors and ligand hereof are blocked to prevent checkpoint ligands from inhibiting the immune system in the tumor tissue or tumor microenvironment. Meanwhile, the mobilizing functional part of the fusion protein is carried to the surface of target cell, so that the activating area is easier to generate effects, and side effects caused by the off-target effect are prevented.

Preferably, amino acid sequence of Anti-PD-1 antibody comprises the sequences shown in SEQ ID NO: 6-9; amino acid sequence of the Anti-CTLA-4 antibody comprises the sequences shown in SEQ ID NO: 10-11; amino acid sequence of Anti-PD-L1 antibody comprises the sequences shown in SEQ ID NO: 12-13.

Preferably, the functional area for conducting activation and amplification on the failing immune cells uses cytokine or functionally-similar mutant, a ligand or functionally-similar mutant of the phenotypic receptor, or an activating antibody to activate and amplify the failing immune cells.

Preferably, cytokine or functionally-similar mutant includes but is not limited to IL-2, IL-15, IL-21; wherein the receptors are mainly expressed on the surface of T cells and NK cells. The cytokine functionally-similar mutant is that on the premise of not changing the basic function of the cytokine, the activation response of the cytokine to target cell is increased and the effect on non-target cell is reduced by amino acid sequence's mutation or by just utilizing polypeptide in the area. For EMBODIMENT, through the changes of the amino acid sequence of IL-2, mutants may reduce the activation with T-regulatory cell to reduce effects on non-target cell and organs, thereby reducing side effects in clinical application.

Preferably, ligands or functionally-similar mutants of the phenotypic receptor include but are not limited to 4-1BBL and OX-40L. activating receptors on the surface of immune cells can be combined with corresponding ligands to achieve the purposes of conducting activation and amplification on target cell by activation and signal transmission; functionally-similar mutants thereof may mutate by amino acid sequence or only include the portion of functional area, which aims to alter the affinity or partial function with the receptor.

Preferably, the activating antibody comprises the antibodies against 4-1BB, XO-40L, CD28, CD3 and CD27. And by combining with the activating site on the activating receptor, the activating antibody can achieve the function similar to that of the ligand and the active signal is stimulated to achieve the purpose of amplifying the target cell.

Preferably, the amino acid sequence of IL-2 is as shown in SEQ ID NO: 14; and amino acid sequence of IL-15 is as shown in SEQ ID NO: 15; amino acid sequence of IL-21 is as shown in SEQ ID NO: 16.

Preferably, amino acid sequence of 4-1BBL is as shown in SEQ ID NO: 17; and amino acid sequence of OX-40L is as shown in SEQ ID NO: 18.

Preferably, amino acid sequence of antibody against 4-1BB comprises the sequence shown in SEQ ID NO: 19-20; wherein amino acid sequence of Anti-XO-40L antibody comprises the sequence shown in SEQ ID NO: 21-22.

Preferably, the area for recognizing the failing immune cells uses Anti-PD-1 antibody to recognize the phenotypic receptor hereof. And IL-2 is used for activating the failing immune cells in the area for conducting activation and amplification on the failing immune cells.

Preferably, fusion protein for restoring the functions of failing immune cells is prepared according to the following steps of:

step 1) forming the heavy chain structural gene of fusion protein by connecting a C-terminal of heavy chain of Anti-human PD-1 antibody with the N-terminal amino acid sequence of IL-2 through non-functional amino acid;

step 2) transferring heavy chain structural gene of fusion protein together with the synthesized light chain gene of the Anti-PD-1 antibody in step 1 into an expression vector and then transfecting it into hamster ovary cells;

and step 3) placing the hamster ovary cells in step 2 in an incubator for culturing for a period of time, extracting the supernatant, and then purifying it to obtain the recombinant fusion protein.

Preferably, heavy chain of the Anti-human PD-1 antibody is the sequence shown in SEQ ID NO: 6; wherein the light chain of the synthetic Anti-PD-1 antibody is the sequence shown in SEQ ID NO: 7; interleukin 2 is the sequence shown in SEQ ID NO: 14; the amino acid sequence of non-functional amino acid is SGGGGSGGGGSGGGGSG; heavy chain structural gene of fusion protein is the sequence shown in SEQ ID NO: 23; and the expression vector is a eukaryotic expression vector pcDNA 3.1.

Preferably, the failing immune cells are at least one kind of the failing specific T cells and failing NK cells.

The invention also provides an application of fusion protein for restoring the functions of failing immune cells, and the application of fusion protein is medically used for non-diagnostic or non-therapeutic purposes.

Preferably, the application is single application of the fusion protein or a combined application hereof with chemotherapy, targeting drugs, antibody drugs and cell therapy, so as to be used for the preparation of the medicament for treating the disease induced by immune cell failure.

Preferably, the diseases include cancer and chronic viral infection disease.

Preferably, the cancer comprises renal cell carcinoma, melanoma, lymphoma, colorectal cancer, liver cancer, ovarian cancer, head and neck squamous cell carcinoma, bladder cancer, lung cancer; wherein viruses of the chronic viral infection disease include HIV, HBV, HCV, EBV, HPV and CMV.

Compared with the prior art, beneficial effects of the present invention are as follows:

The fusion protein provided by the present invention can serve demands of immune recovery of patients, and the recombinant fusion protein can not only recognize failing immune cells, but also increase the amount and restore the functions thereof. Moreover, the clinical application can enhance the functions of inhibiting tumor's growth and controlling virus infection, and have a great clinical prospect and wide application range.

SPECIFIC EMBODIMENTS

The present invention provides a fusion protein for restoring the function of the failing immune cell, comprising a functional area for recognizing the failing immune cell and a functional area for conducting activation and amplification on the failing immune cell, and the two functional areas are connected through a non-functional amino acid fragment with a certain length; and the invention also provides the application of the fusion protein in preparation of a medicament for treating diseases caused by immune cell failure.

Hereinafter, specific embodiments of the present invention shall be clearly and completely described with reference to the accompanying drawings and embodiments. However, the following embodiments are merely to more clearly illustrate the technical solutions of the present invention, without limiting the scope of the present invention.

Embodiment 1

The present embodiment is for gene construction and production purification of recombinant fusion protein.

Figure 1:
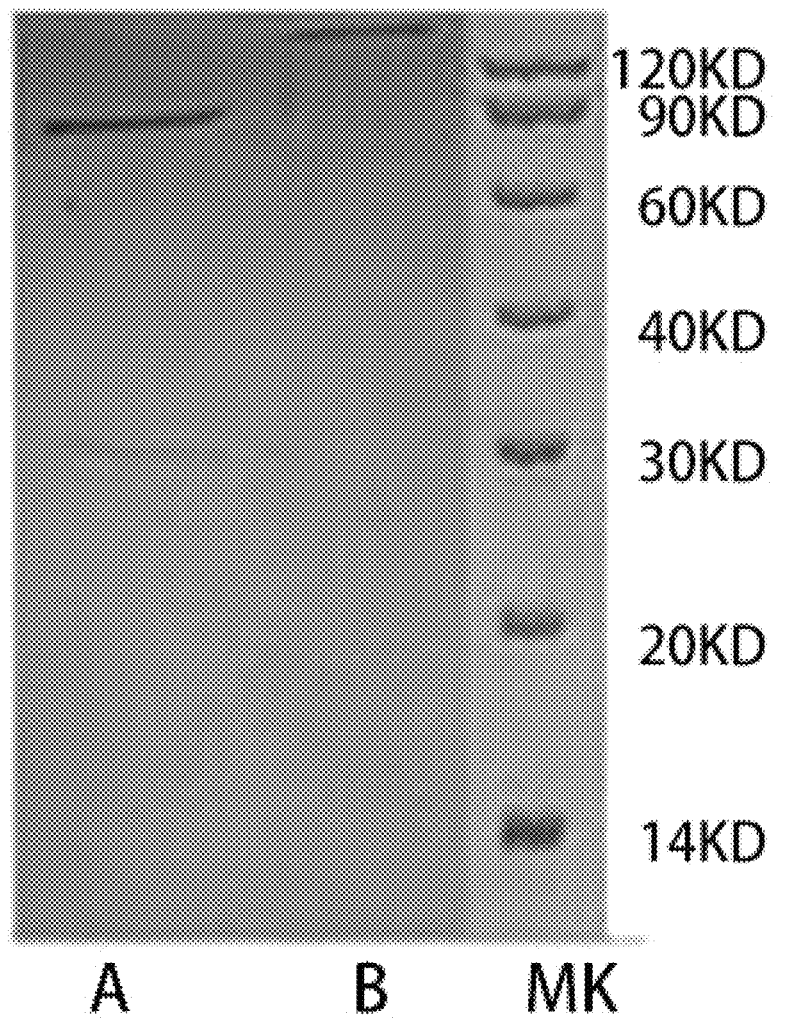
FIG. 1 is a gel electrophoresis analysis view of recombinant fusion protein prepared in one embodiment of the present invention, wherein lane A is the protein in reduced state; lane B is the protein in non-reduced state; and MK is the marker of standard molecular weight of the protein.

N-terminal amino acid sequence of C-terminal of heavy chain of Anti-human PD-1 antibody (SEQ ID NO: 6) and N-terminal amino acid sequence of interleukin 2 (SEQ ID NO: 14) were linked by 17 non-functional amino acids (SGGGGSGGGGSGGGGSG, SEQ ID NO: 24) through gene synthesis, enzyme digestion and further cloning, so as to form heavy chain structural gene of fusion protein (SEQ ID NO: 23) and it was then transferred into expression vector pcDNA3.1 of eukaryote; light chain (SEQ ID NO: 7) gene of the Anti-PD-1 antibody was transferred into expression vector pcDNA3.1 of eukaryote through gene synthesis, enzyme digestion and further cloning. Lastly, heavy chain expression vector and light chain expression vector of the fusion protein were simultaneously transfected into Chinese hamster ovary cell (CHO); wherein the transfected cells were cultured in the incubator at 37° C. with 5% $CO_2$. Upon cultured for 72 hours, the obtained supernatant was further purified by Protein A affinity chromatography, and eventually the purified protein was the bifunctional recombinant fusion protein. In the meantime, non-fusion protein was prepared according to Anti-PD-1 antibody sequence (SEQ ID NO: 6, SEQ ID NO: 7) and interleukin 2 sequence (SEQ ID NO: 14) by methods above to be a control for the assay. The molecular weight of purified protein (seen also FIG. 1) was confirmed by electrophoresis detection, which proved that the recombinant fusion protein designed by the present invention can be produced by CHO cell. In the end, the protein whose concentration was measured by a spectrophotometer, was diluted in PBS and used for further activity assay as well as function study in vitro and in vivo.

Embodiment 2

The embodiment is an activity and function assay of bifunctional recombinant fusion protein to extracellular culture of human PBMC.

Figure 2:
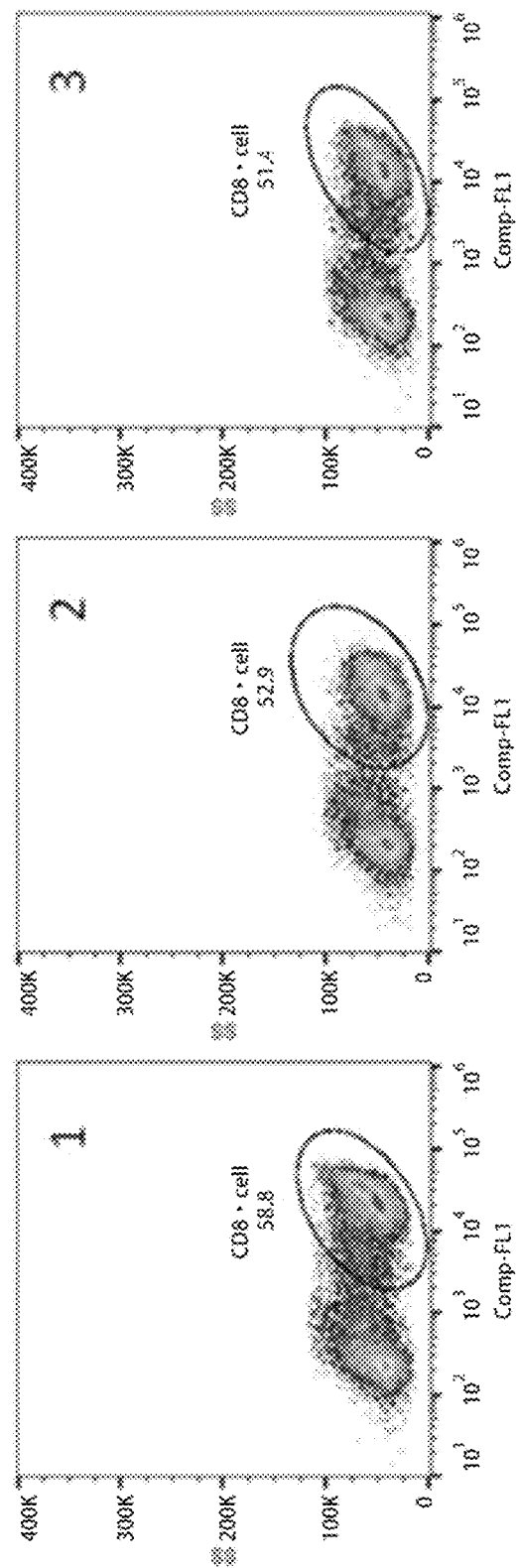
FIG. 2 is a diagram of the ratio of CD8+ T cell tested in vitro by recombinant fusion protein human PBMC prepared in one embodiment of the present invention, wherein the fusion protein group is part 1 of FIG. 2, and Anti-PD-1 antibody group is part 2 of FIG. 2, the interleukin 2 group is part 3 of FIG. 2.
Figure 3:
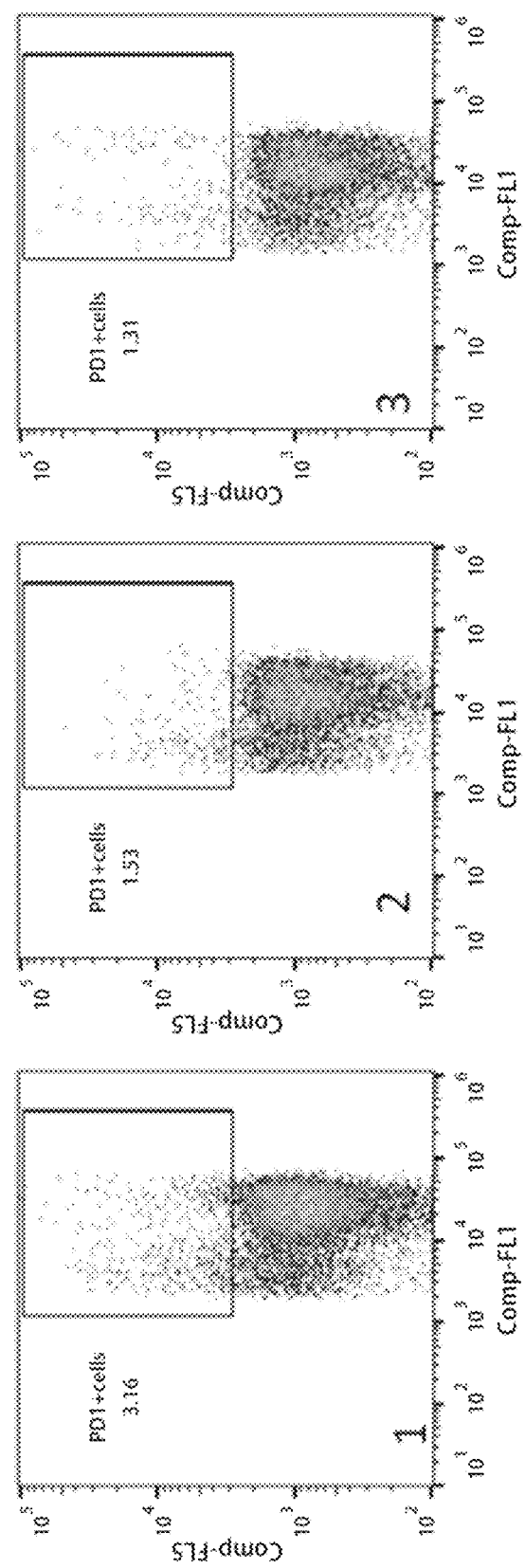
FIG. 3 is a diagram of the ratio of PD-1+ cell in CD8+ T cells tested in vitro by recombinant fusion protein human PBMC prepared in one embodiment of the present invention wherein the fusion protein group is part 1 of FIG. 3, and Anti-PD-1 antibody group is part 2 of FIG. 3, the interleukin 2 group is part 3 of FIG. 3.

Human peripheral blood was isolated and purified by lymphocyte density gradient centrifugation (Ficoll), and cell density was diluted to $5 \times 10^6$/mL with X-Vivo15 Medium in 24-well plate; after adding test protein, the final concentration of solution was 2 μg/mL. then the solution was cultured at 37° C. for 30 minutes and X-Vivo15 Medium was changed after centrifugation to a final cell density of $5 \times 10^5$/mL. After that then it was cultured in an incubator at 37° C. with 5% $CO_2$ for 72 hours prior to use and the collected cells were stained with CD8 and Anti-PD-1 antibody for phenotypic determination and data analysis by flow cytometer. As shown in FIG. 2, fusion protein treatment (seen also part 1 of FIG. 2) significantly increased the proportion of CD8+ cell among cultured cell (58.8%, 52.9%, 51.4%) compared to unfused Anti-PD-1 antibody (seen also part 2 of FIG. 2) and interleukin 2 (seen also part 3 of FIG. 2). Meanwhile, as shown in FIG. 3, the proportion of PD-1+ cells to CD8+ T cells in the fusion protein treated group after culture was 3.16% (seen also part 1 of FIG. 3), while the Anti-PD-1 antibody treated group hereof was 1.53% (seen also part 2 of FIG. 3) and the interleukin 2 treated group hereof was 1.31% (seen also part 3 of FIG. 3). Thereby, fusion protein can significantly enhance the expansion of failing cell (PD-1+) among CD8+ T cell. Experiments proved that the recombinant fusion protein designed in the present invention can not only selectively expand T cell of CD8+, but also directionally amplify failing CD8+ PD-1+ cell, which is for intended purpose of the fusion protein.

Embodiment 3

The embodiment illustrates effects of bifunctional recombinant fusion protein on effector cell in vivo.

Mice were injected intraperitoneally with either fusion protein (4 μg/mouse/day) or interleukin 2 (40 μg/mouse/day) or PBS (control group) for 3 consecutive days, respectively.

Figure 4:
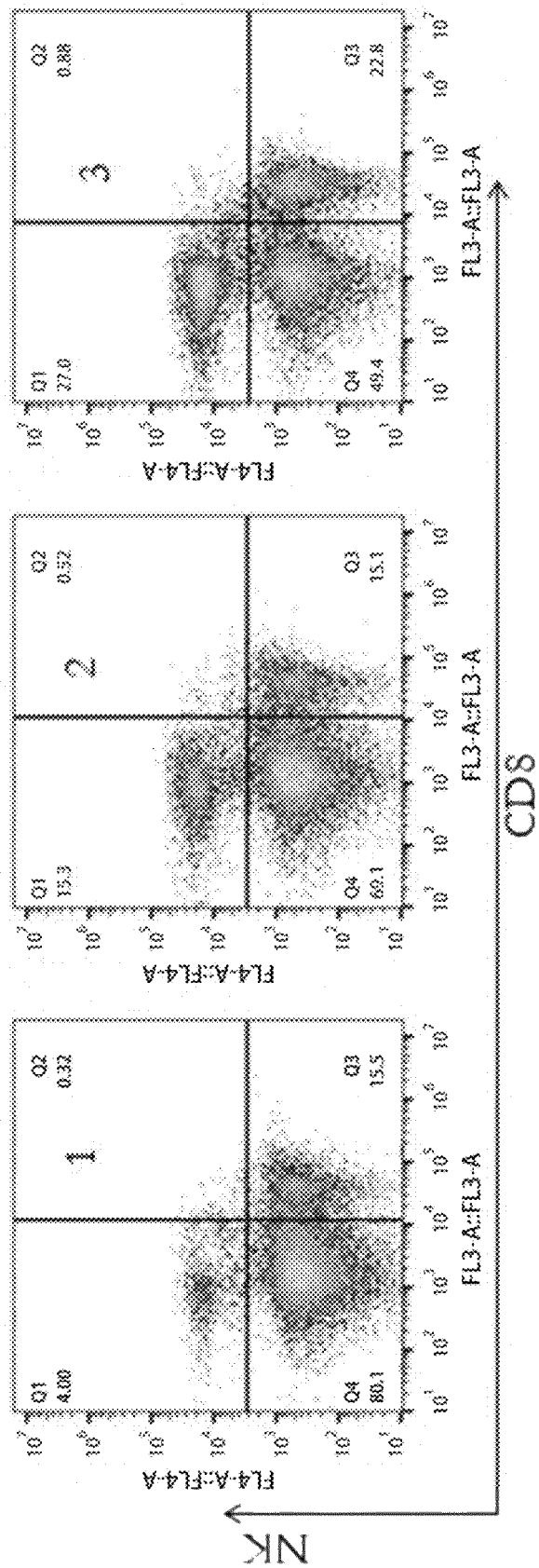
FIG. 4 is a diagram of the ratio of CD8+ T cell and NK cell in peripheral blood lymphocytes tested in vivo in a recombinant fusion protein mouse according to one embodiment of the present invention, wherein the fusion protein group was part 3 of FIG. 4, and the interleukin 2 group is part 2 of FIG. 4, the PBS control group is part 1 of FIG. 4.

On day 4, peripheral blood was taken from the tail and detected after being stained with anti-mouse CD8 and NK1.1 flow antibody wherein the data analysis is shown in FIG. 4. The recombinant fusion protein significantly increased the proportion of NK cell in lymphocyte (seen also part 3, 27.0% of FIG. 4) compared with the control group (seen also part 1, 4.0% of FIG. 4) and the interleukin 2 group (seen also part 2, 15.3% of FIG. 4). Meanwhile, in CD8+ T cell, protogenic interleukin 2 did not increase the proportion of CD8+ cell (seen also part 2, 15.1% of FIG. 4) as compared to the control group (seen also part 1, 15.5% of FIG. 4), whereas the proportion of CD8+ T cell in peripheral blood of fusion protein-treated mice (part 3 of FIG. 4) reached 22.8%. In vivo tests illustrated that the immune response of the synthetic fusion protein in the present invention can far exceed that of protogenic non-fusion protein even at doses of only 10% of protogenic IL-2.

Embodiment 4

The embodiment is application of bifunctional recombinant fusion protein in preparation of the medicament for treating diseases induced by immune cell failure. Wherein the bifunctional recombinant fusion protein can be applied alone or combined with chemotherapy, targeting drugs, antibody drugs and cell therapy, which aims to prepare drugs for treating diseases caused by immune cell failure, for instance, drugs for treating cancer and those for treating chronic viral infection and the like.

According to the embodiments, fusion protein for restoring the functions of the failing immune cell can recognize the failing immune cell, as well as activating and amplifying the recognized immune cell, restoring immune cell's function of killing antigen positive cell. Genesis and diffusion of tumor and the chronic virus infection are on account of immune cell failure and immunological tolerance, while the function of restoring of the failing immune cell can enhance the anti-tumor and anti-chronic viral infection capabilities of organisms. In conclusion, the clinical application of the above fusion protein, which can enhance the functions of inhibiting tumor growth and controlling virus infection, has good clinical prospect and wide application range.

The specific embodiments of the present invention have been described in detail above, but by way of example only, the invention is not limited to the specific embodiments described above. For those skilled in the art, any equivalent modifications and alterations to the invention are within the scope of this invention. Accordingly, equivalent alterations and modifications are within the scope of the invention if not departing from the spirit and scope thereof.

The invention claimed is:

1. A bifunctional recombinant protein for restoring the ability of exhausted T cells and/or NK cells to kill antigen positive cells, comprising a light chain of an antibody specific to human PD-1 and a fusion protein which comprises a heavy chain of the antibody specific to human PD-1, wherein the amino acid sequence of the light chain is SEQ ID NO: 7 and the amino acid sequence of the fusion protein is SEQ ID NO: 23.

2. The bifunctional recombinant protein according to claim 1, wherein the bifunctional recombinant protein is prepared according to the following steps of:

(1) forming a structural gene encoding the fusion protein by connecting a nucleic acid encoding the heavy chain of the antibody specific to human PD-1 with the nucleic acid encoding IL-2, such that the (-terminus of the heavy chain is linked to the N-terminus of IL-2 by a non-functional amino acid sequence, and transferring the structural gene encoding the fusion protein into an expression vector;

(2) synthesizing a structural gene encoding the light chain of the anti-PD-1 antibody, and transferring the structural gene encoding the light chain into an expression vector;

(3) simultaneously transfecting the expression vectors obtained in steps (1) and (2) into CHO cells;

(4) culturing the CHO cells transfected with the expression vectors for a period of time; and (5) obtaining a supernatant from the culture of step (4) and purifying the recombinant protein from the supernatant.

3. The bifunctional recombinant protein according to claim 2, wherein expression vector is a eukaryotic expression vector pcDNA3.1.

4. A medicament comprising the bifunctional recombinant protein of claim 1.

* * * * *